United States Patent [19]

Molnar, IV

[11] Patent Number: 4,826,483
[45] Date of Patent: May 2, 1989

[54] NON-REUSABLE SYRINGE

[75] Inventor: William F. Molnar, IV, Houston, Tex.

[73] Assignee: Paul F. Boyd, Houston, Tex. ; a part interest

[21] Appl. No.: 190,557

[22] Filed: May 5, 1988

[51] Int. Cl.⁴ ............................................. A61M 5/00
[52] U.S. Cl. .................. 604/110; 604/210; 604/224
[58] Field of Search ............... 604/110, 224, 218, 208, 604/209, 210, 220, 221, 222, 228, 211

[56] References Cited
U.S. PATENT DOCUMENTS

| | | | |
|---|---|---|---|
| 2,707,954 | 5/1955 | Kas, Sr. | 604/210 |
| 4,233,975 | 11/1980 | Yerman | 604/110 |
| 4,367,738 | 1/1983 | Legendre et al. | 604/218 X |
| 4,391,272 | 7/1983 | Staempfli | 604/110 |
| 4,493,703 | 1/1985 | Butterfield . | |
| 4,687,467 | 8/1987 | Cygielski . | |
| 4,699,614 | 10/1987 | Glazier . | |
| 4,710,170 | 12/1987 | Haber et al. . | |

Primary Examiner—John D. Yasko
Attorney, Agent, or Firm—Fulbright & Jaworski

[57] ABSTRACT

A syringe having a cylinder and a piston longitudinally and rotationably movable in the cylinder. First and second sets of one-way ratchet shoulders and ratchet keys are provided between the cylinder and the piston in which the first set of shoulders and key, when engaged, allow movement of the piston in one longitudinal direction but prevent movement in the opposite second direction. The second set of shoulders and key, when engaged, allow movement of the piston in the second direction but prevent movement in the first direction. A rotational control between the piston and the cylinder provides for sequentially disengaging and engaging the first and second sets of ratchet shoulders and keys upon rotation of the piston relative to the cylinder for operating the syringe for a single cycle.

9 Claims, 3 Drawing Sheets

U.S. Patent May 2, 1989 Sheet 1 of 3 4,826,483
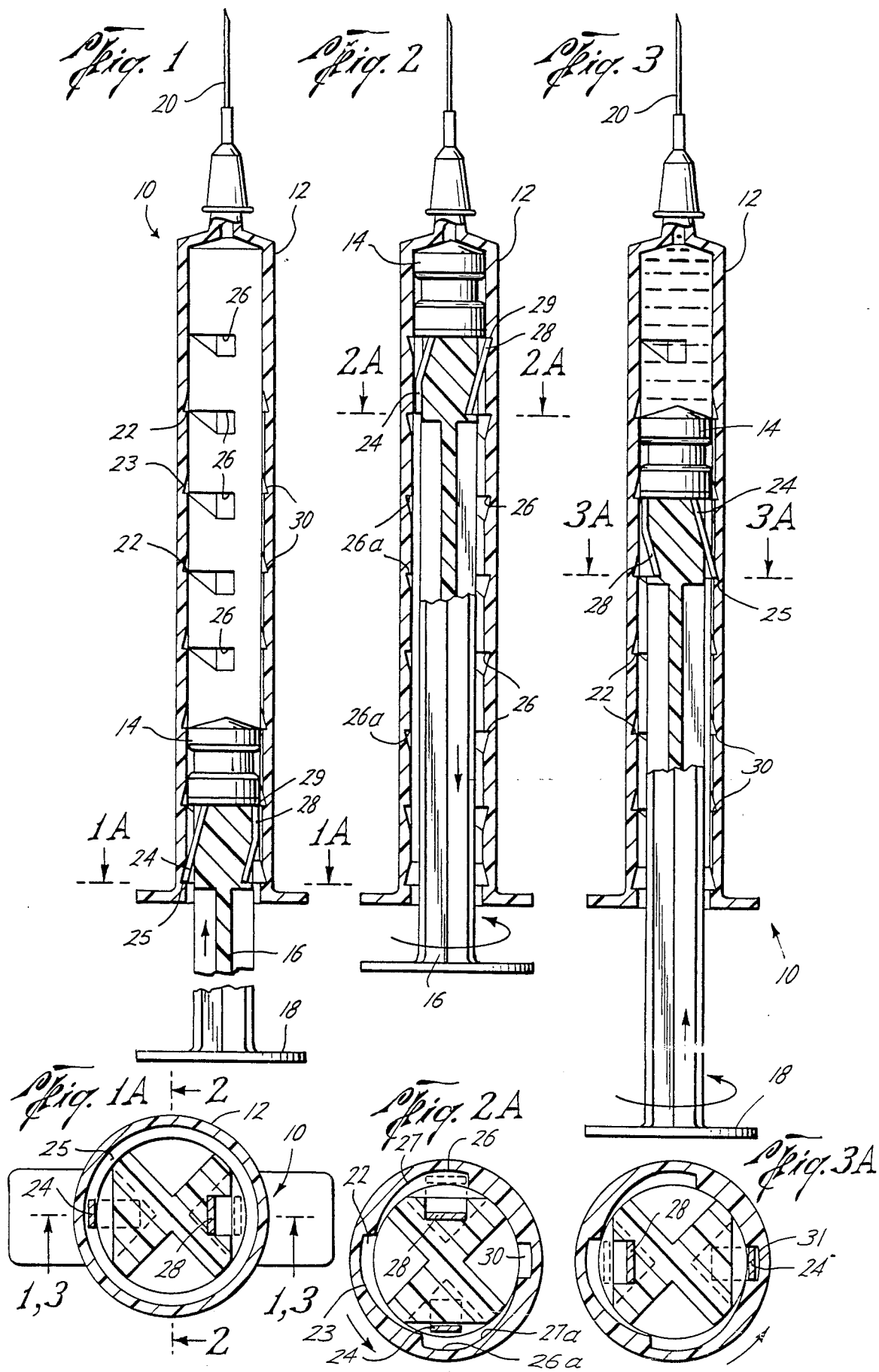

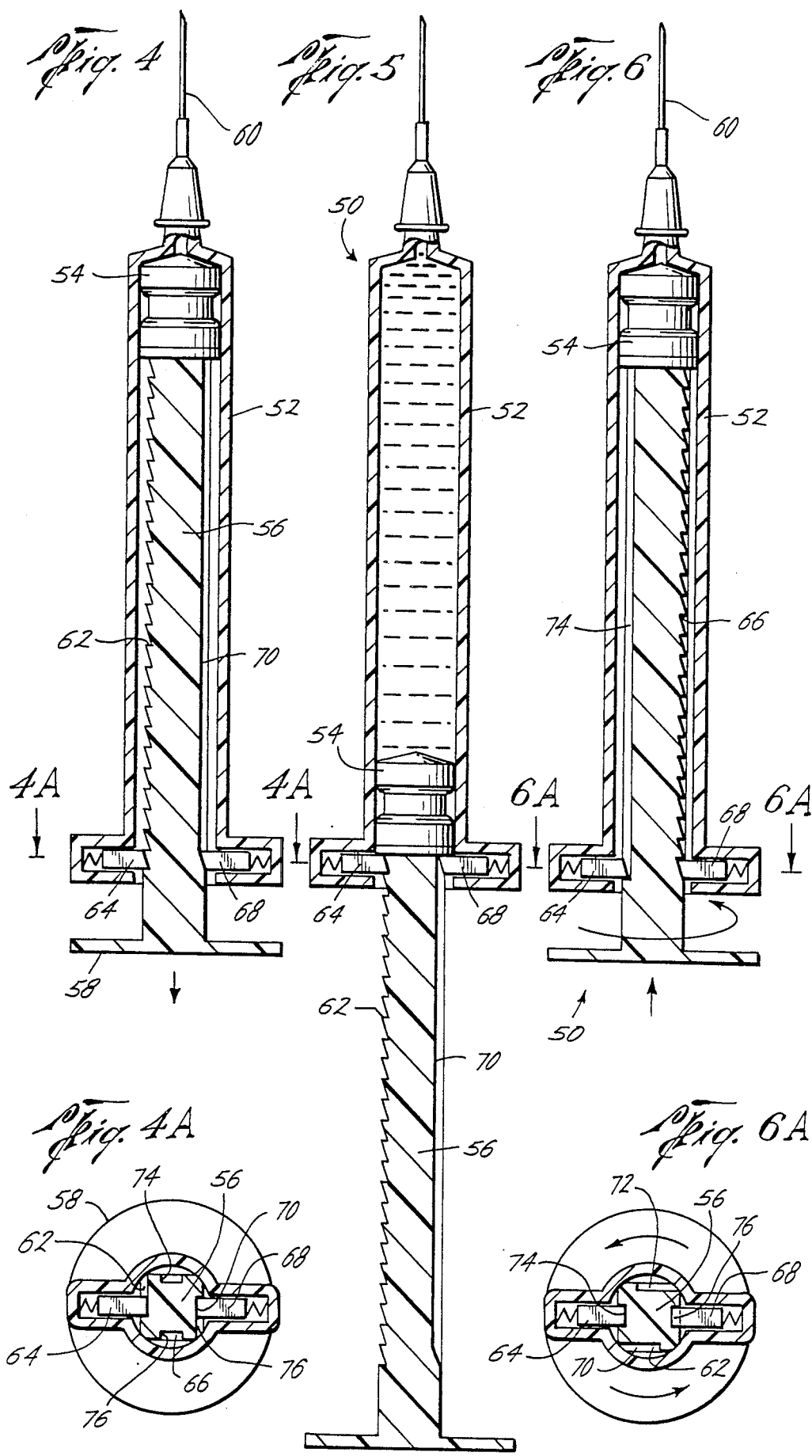

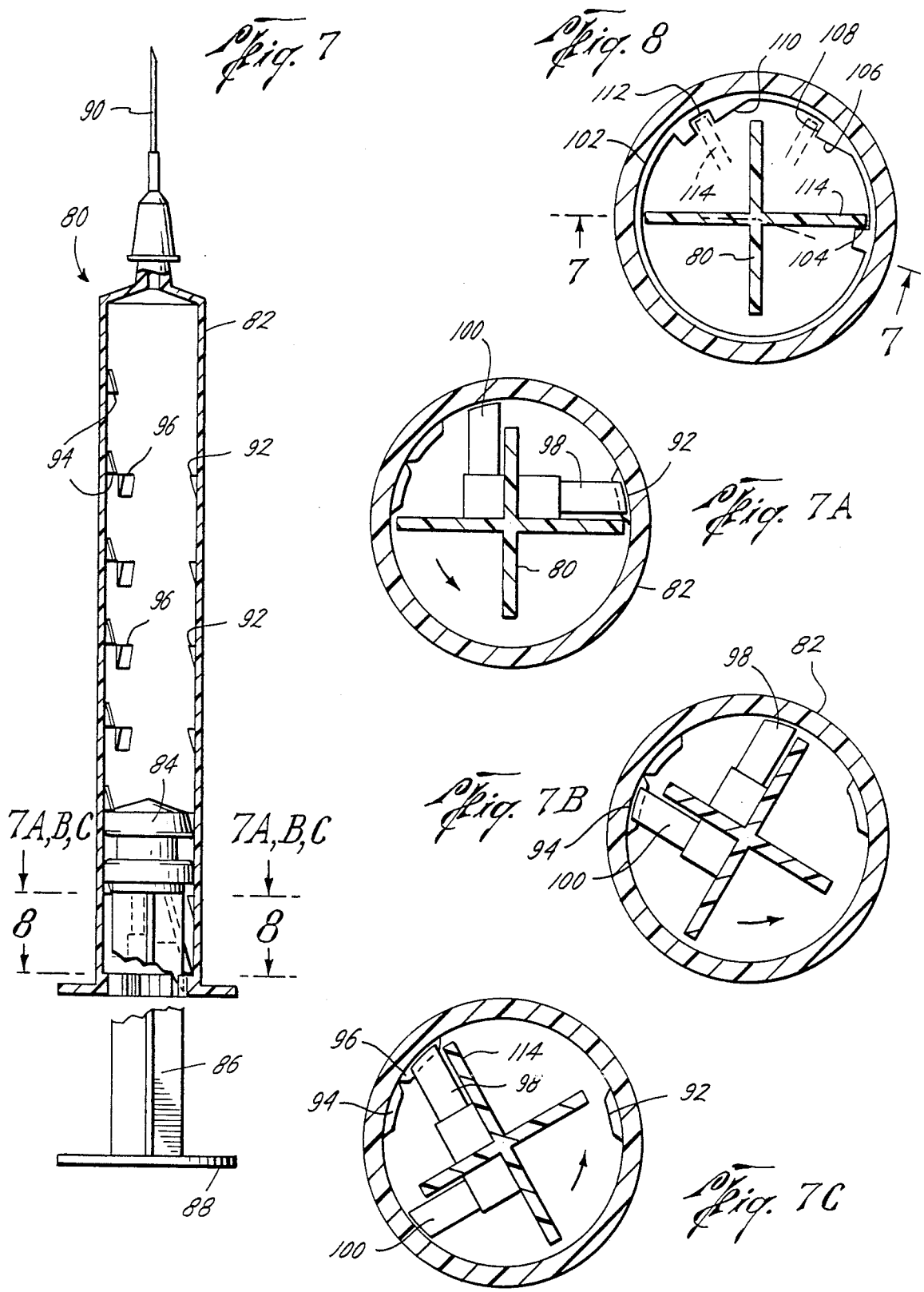

NON-REUSABLE SYRINGE

BACKGROUND OF THE INVENTION

It is known to provide a medical syringe which can only be used a single time. This is necessary to prevent the transmission of diseases from one person to another person by reusing a syringe or for undesirably mixing different medical injections on reuse.

The present invention is directed to an improved non-reusable syringe which is easy to use, which will perform the injection function satisfactorily and will accurately measure liquids, but which will insure that it can only be used a single time.

SUMMARY

The present invention is directed to a non-reusable syringe having a cylinder and a piston movable in the cylinder. First one-way coacting means are provided between the piston and the cylinder allowing movement of the piston relative to the cylinder in one direction but not in the opposite second direction. Second one-way coacting means between the piston and the cylinder allow movement of the piston relative to the cylinder in the second direction, but not in the first direction. Said first and second one-way means are circumferentially displaced from each other. Rotational control means are provided between the piston and the cylinder for sequentially disengaging and engaging said first and second one-way coacting means upon rotation of the piston relative to the cylinder for allowing operation of the syringe for a single cycle.

A further object of the present invention is wherein the rotational control means include a recess and a key which when mated prevent further rotation between the piston and cylinder.

Still a further object of the present invention is wherein the rotational control means allows rotation between the Piston and cylinder in a single rotational direction.

Yet a still further object of the present invention is wherein the rotational control means includes a ratchet key and a plurality of recesses having a vertical shoulder on one edge of the recess and a tapering periphery extending from the shoulder.

Still a further object of the present invention is wherein the rotational control means includes a key on one of the piston and cylinder and a surface coacting with the key on the other piston and cylinder and said surface includes a stop recess, a plurality of vertical control shoulders and a guide surface extending from each of the control shoulders.

Still a further object is the provision of a non-reusable syringe having a cylinder with a piston telescopically and rotationally movable in the cylinder with a handle connected to the piston for longitudinally and rotationally moving the piston relative to the cylinder A first set of one-way ratchet shoulders and a first ratchet key are provided with the shoulders being on one of the cylinder and piston and the first key being on the other of the cylinder and piston. The first set of shoulders and first key, when engaged, allow movement of the Piston in one longitudinal direction relative to the cylinder, but prevent movement in the opposite direction. A second set of one-way ratchet shoulders and a second ratchet key are provided with the second shoulders being on one of the cylinder and piston and the second key being on the other of the cylinder and piston. The second set of shoulders and said second key, when engaged, allow movement of the piston in the second longitudinal direction but prevent movement in the first direction. Rotational control means between the piston and cylinder allow sequential operation of the syringe but only for operating the syringe in a single cycle. The rotational control means includes a recess for receiving one of the keys for preventing further rotation between the piston and the cylinder. Preferably the keys are of different sizes whereby only one of the keys will fit into the recess.

Another object is the provision of one or more additional sets of one-way ratchet shoulders spaced from the other sets of ratchet shoulders.

Other and further objects, features and advantages will be apparent from the following description of the presently preferred embodiments of the invention, given for the purpose of disclosure and taken in conjunction with the accompanying drawings.

BRIEF DESCRIPTION OF THE DRAWINGS

FIG. 1 is an elevational view, Partly in cross section, of one embodiment of the present invention with the piston retracted, FIG. 1A is a cross-sectional view taken along the line 1A—1A of FIG. 1, FIG. 2 is a cross-sectional view taken along the line 2—2 of FIG. 1A with the piston extended into the cylinder, FIG. 2A is a cross-sectional view taken along the line 2A—2A of FIG. 2, FIG. 3 is a cross-sectional view taken along the line 3—3 of FIG. 1A showing the syringe expelling liquid, FIG. 3A is a cross-sectional view taken along the line 3A—3A of FIG. 3, FIG. 4 is an elevational view, partly in cross section, illustrating another embodiment of the Prevent invention, FIG. 4A is a cross-sectional view taken along the line 4A—4A of FIG. 4, FIG. 5 is an elevational view, partly in cross section, of the apparatus of FIG. 4 shown in Position after drawing liquid into the syringe, FIG. 6 is an elevational view, partly in cross section, of the apparatus of FIGS. 4 and 5 after expelling the liquid from the syringe, FIG. 6A is a cross-sectional view taken along the line 6A—6A of FIG. 6, FIG. 7 is an elevational view, partly in cross section, of another embodiment of the present invention, FIG. 7A, 7B nd 7C are cross-sectional views taken along the line 7A—7A, 7B—7B, and 7C—7C, respectively, but in different rotational positions, and FIG. 8 is a cross-sectional view taken along the line 8—8 of FIG. 7.

DESCRIPTION OF THE PREFERRED EMBODIMENT

Referring now to FIGS. 1-3, a first embodiment of the present invention is shown in which a syringe, generally indicated by the reference numeral 10, is shown which is capable of expelling air from the syringe for Pressurizing a liquid container, drawing a measured amount of liquid into the syringe, and expelling the liquid from the syringe. The syringe 10 generally includes a cylinder 12, a piston 14 which is rotatably and longitudinally movable in the cylinder 12, and includes a piston rod 16 connected to a handle 18 for longitudinally and rotationally moving the piston 14 relative to the cylinder 12. In addition, a conventional syringe needle 20 is connected to the cylinder 12.

As shown in FIG. 1, the piston 14 is shown in the retracted Position with air filling the cylinder 12 for injection into a liquid container for pressuring the container. First one-way coacting means is provided between the piston and cylinder allowing movement of the piston relative to the cylinder in one direction, but not in the opposite second direction. For example, a first set of upwardly facing one-way ratchet shoulders 22 coact with a first end 25 of a ratchet key 24. While the shoulders 22 and key 24 may be on either of the cylinder 12 and piston 14, as best seen in FIG. 1, the shoulders 22 are longitudinally aligned and recessed in the inner Periphery of the cylinder 14 for coacting with the first ratchet key 24. Thus the first one-way coacting means, when engaged, allows the piston 14 to move inwardly in the cylinder 12 but prevents the piston 14 from moving in the opposite second direction.

A second one-way coacting means is also provided between the piston and cylinder allowing movement of the piston relative to the cylinder in the second direction but not in the first direction. Thus, a second set of one-way ratchet shoulders 26, facing downwardly, are Provided on one of the cylinder 12 and piston 14, here shown as in the cylinder 12, longitudinally recessed in the cylinder 12. A second ratchet key 28 having an end 29 is provided connected to the other of the cylinder 12 and piston 14 here shown as the piston 14 for coacting with the shoulders 26 for allowing movement of the piston 14 in a direction outwardly from the cylinder 12, but prevents inward movement of the piston 14 into the cylinder 12. Preferably, as best seen in FIGS. 2 and 2A, two sets of downwardly facing ratchet shoulders 26 and 26A are provided spaced apart 180° in the cylinder 12. It is also noted that the upwardly facing shoulders 22 are circumferentially spaced from the shoulders 26 and 26A and the ratchet key 24 is circumferentially spaced from the ratchet key 28.

In the present embodiment, as best seen in FIG. 3, another set of upwardly directed ratchet teeth 30 is provided in the cylinder 12 180° circumferentially spaced from the first upwardly directed set of ratchet teeth 22.

Referring to Figs. 1A, 2A and 3A, it is to be noted that the width of the first ratchet key 24 is less than the width of the second ratchet key 28 and that the width of the recesses 31 above the shoulders 30 are sized to coact with the smaller ratchet key 24 but will not accept the width of the ratchet key 28. In addition, the recesses 23 above ratchet keys 22, the recesses 27 above the ratchet teeth 26, and the recesses 27a below the ratchet teeth 26a, include tapering peripheries extending inwardly to the inner periphery of the cylinder 12 for allowing the ratchet keys to be rotated out of the recesses 23, 27 and 27a.

Referring now to FIG. 1, the piston 14 is in a rotational position relative to the cylinder 12 with the key 24 aligned with the shoulders 22 whereby the handle 18 may be actuated to longitudinally move the piston 14 into the cylinder 12 for expelling air out of the needle 20. The end 25 of the ratchet key 24 will ratchet past the shoulders 22 and the end 29 of ratchet key 28 will ratchet Past the shoulders 30 for expelling the air. However, when the piston 14 reaches it inward extent of travel, it cannot be pulled outwardly as the end 25 of the ratchet key 24 will engage the shoulders 22 for preventing such longitudinal movement.

Therefore, as best seen in FIG. 2 and 2A, the piston 14 is then rotated 90° to align the keys 24 and 28 with the sets of downwardly facing shoulders 26a and 26, respectively. Thereafter, the handle 18 may be longitudinally moved to withdraw the piston 14 from the cylinder 12 and thereby draw liquid into the cylinder 12. It is to be noted that the shoulders 26 are preferably positioned to correspond to cc liquid measurements to allow the operator to accurately measure the desired volume of liquid both by sight and feel. Now, with the piston 14 in a retracted position, the piston cannot again be moved longitudinally inwardly in the cylinder 12 as the end 29 of the key 28 would encounter the downwardly directed shoulders 26.

Therefore, the piston 14 is again rotated 90°, as best seen in FIGS. 3 and 3A, and is pushed inwardly into the cylinder to expel the liquid therein. In the Position shown in FIGS. 3 and 3A, the piston may be moved longitudinally as the keys 24 and 28 are now aligned with the sets of ratchet keys 22 and 30 and can move inwardly. However, as best seen in FIG. 3A, the ratchet key 24 will be engaged in the recess 31 and therefore no further rotation of the piston 14 relative to the cylinder 12 is possible and no further longitudinal withdrawal of the piston 14 is possible as the end 25 of the key 26 will engage the upwardly directed shoulders 30 in the cylinder. The cycle of operation is complete and the piston 14 is locked into the cylinder 12 and thus is not reusable.

Referring now to FIG. 4–6, another embodiment is best seen and indicated by the reference numeral 50 which includes a cylinder 52, a piston 54 which includes piston rods 56 connected to a handle 58 and a needle 60. In the particular embodiment here shown the syringe 50 is used in those operations which do not require that air be expelled into a closed container for pressurizing liquid. Instead, in its initial position, the piston 54 is already extended inwardly in the cylinder 52.

A first one-way coating means is provided between the piston and the cylinder such as a first set of one-way ratchet shoulders 62, on one of the pistons 50 or cylinder 52, here shown as being on the piston rod 56, and a first ratchet key 64. Thus when the key 54 is engaged with the shoulder 62, the piston 54 may be longitudinally moved away from the needle 60 for drawing liquid into the cylinder 52 but is prevented from movement inwardly into the cylinder 52.

Second one-way coacting means are provided between the piston and the cylinder such as a second set of one-way ratchet shoulders 66 on the shaft 56 and circumferentially positioned 90° away from the first set of ratchet shoulders 62. A second ratchet key 68 is Provided and when engaged with the second set of ratchet shoulders 66 allow inward movement of the piston 54 into the cylinder 52 but prevents withdrawn of the piston 54 from the cylinder 52. However initially the second ratchet key 68, as best seen in FIGS. 4 and 5, is in engagement with a smooth surface 70 on the piston rod 56.

Referring to FIGS. 4A and 6A, the piston rod 56 is rotatable by the handle 58 from the position shown in FIG. 4A to the Position shown in 6A at which position the rotation of the piston rod 56 is locked. That is, while the piston rod 56 may be rotated, as best seen in FIG. 4A, in a counterclockwise direction from the position shown therein, as the sides 70 and 72, when rotated, will press the keys 64 and 68, respectively, outwardly for allowing such rotation. However, when the piston rod 56 is rotated 90°, recesses 74 and 76 will be engaged by the ratchet keys 64 and 68, respectively, as best seen in FIG. 6A, preventing further rotation of the piston rod 56.

In use, the syringe 50 is shown in its original position in FIG. 4. By withdrawing the handle 56, the piston 54 is retracted from the cylinder 52 to draw in liquid to be injected into the cylinder 52. That is, the ratchet shoulders 62 will ratchet past ratchet key 64 while key 68 will move along the smooth groove 70. After the liquid has been drawn into the cylinder 52 in FIG. 5, the piston rod 56 is rotated 90° in a counterclockwise direction to bring the ratchet shoulders 62 out of engagement with the ratchet key 64 and to bring ratchet shoulders 66 into engagement with ratchet key 68. While this rotationally locks the rotational position of the Piston rod 66, the handle 58 may be longitudinally moved to inject the liquid out of the cylinder 62.

Since the piston rod 56 can no longer be rotated and since the shoulder 66 prevents withdrawal of the piston 54 because of the ratchet key 68, the cycle is completed and the syringe is locked in place and therefore is not reusable.

If desired, additional one-way coacting means can be provided for allowing this embodiment to allow the piston 54 to start in a retracted position and pressurize a liquid container.

Referring now to FIGS. 7 and 8, another embodiment is shown of a syringe 80 having a cylinder 82 in which a piston 84 telescopically and rotationally moves and includes a piston rod 86, a handle 88, and a syringe needle 90. A first set of upwardly directed shoulders 92, a second set of downwardly directed shoulders 94 and a third set of upwardly directed shoulders 96 are provided in the cylinder 82.

A first ratchet key 98 is provided connected to the piston rod 80 and a second ratchet key 100 is connected to the piston rod 80.

Referring to FIGS. 7 and 8, a rotational control means 102 is provided having a first stop shoulder 104, an inwardly tapering surface 106, a second stop shoulder 108, a second inwardly tapering surface 110, and a locking recess 112.

The piston rod 86 includes at least one slightly flexible key 114 of a length sufficient to coact with the control means 102.

In use, with the piston 84 retracted as best seen in FIG. 7 and the rotational position of the piston rod 80 as shown in FIGS. 7A and 8, the handle 88 is actuated inwardly to expel the air in the cylinder 82. During the inward movement of the piston 84, the ratchet key 98, as best seen in FIG. 7A, will ratchet over the longitudinally spaced shoulders 92 while the air is being expelled, but will prevent retraction of the piston 84. At the end of the inward stroke, the piston rod 86 is actuated to a position shown in FIG. 7B and in dotted outline in FIG. 8 to align the key 114 against the shoulder 108 and the handle 86 is retracted longitudinally. Ratchet key 100 will now ratchet over the downwardly facing shoulders 94 and ratchet key 98 is free of shoulders. During the downward movement of the piston 84, liquid is drawn into the cylinder 82 through the needle 90. The piston rod 86 is further rotated to bring the key 114 into the position shown in FIG. 7C and in dotted outline in FIG. 8 and into locking recess 112 (FIG. 8). While the piston rod 86 is locked against further rotational movement, it is now moved inwardly longitudinally and the ratchet key 98 will ratchet over the set of shoulders 96 while the piston 84 ejects liquids from the cylinder 82. Thereafter, the syringe is locked against further movement.

The present invention, therefore, is well adapted to carry out the objects and attain the ends and advantages mentioned as well as others inherent therein. While presently preferred embodiments of the invention have been given for the purpose of disclosure, numerous changes in details of construction will be readily apparent to those skilled in the art and which are encompassed within the spirit of the invention and the scope of the appended claims.

What is claimed is:

1. A non-reusable syringe comprising,
   a cylinder,
   a piston movable in said cylinder,
   first one-way coacting means between the piston and the cylinder allowing movement of the piston relative to the cylinder in one direction but not in the opposite second direction,
   second one-way coacting means between the piston and cylinder allowing movement of the piston relative to the cylinder in the second direction but not in the first direction,
   said first and second one-way means circumferentially displaced from each other,
   rotational control means between said piston and said cylinder for sequentially disengaging and engaging said first and second one-way coacting means upon rotation of the piston relative to the cylinder for allowing operation of the syringe a single cycle.

2. The apparatus of claim 1 wherein the rotational control means includes a recess and a key which when mated prevent further rotation between the piston and the cylinder.

3. The apparatus of claim 1 wherein the rotational control means allows rotation between the piston and cylinder in a single rotational direction.

4. The apparatus of claim 1 wherein the rotational control means includes a ratchet key and a plurality of recesses each having a vertical shoulder on one edge of the recess and a tapering periphery extending from each shoulder.

5. A non-reusable syringe comprising,
   a cylinder,
   a piston telescopically and rotationally movable in the cylinder,
   a handle connected to the piston for longitudinally and rotationally moving the piston relative to the cylinder,
   a first set of one-way ratchet shoulders and first ratchet key, said shoulders being on one of the cylinder and piston and the first key being on the other of the cylinder and piston, said first set of shoulders and first key, when engaged, allowing movement of the piston in one longitudinal direction relative to the cylinder, but preventing movement in the opposite second direction,
   a second set of one-way ratchet shoulders and a second ratchet key, said second shoulders being on one of the cylinder and piston and the second key being on the other of the cylinder and piston, said second set of shoulders and said second key, when engaged, allowing movement of the piston in the second longitudinal direction, but preventing movement in the first direction, said first and second sets of ratchet shoulders and ratchet keys being circumferentially spaced from each other, respectively, and rotational control means between said piston and said cylinder for sequentially disengaging and engaging said first shoulders and key and said second shoulders upon rotation of the piston relative to the cylinder for operating the syringe a single cycle.

6. The apparatus of claim 5 includes, one of more additional sets of one-way ratchet shoulders circumferentially spaced from the other sets of ratchet shoulders.

7. The apparatus of claim 5 wherein the rotational control means includes a recess for receiving one of said keys for preventing further rotation between the piston and the cylinder.

8. The apparatus of claim 7 wherein said keys are of different sizes whereby only said one key will fit into said recess.

9. The apparatus of claim 5 wherein the rotational control means includes a key on one of the piston and cylinder and a surface coacting with said key on the other of the piston and cylinder, said surface including a stop recess, a plurality of vertical control shoulders and a guide surface extending from each of the control shoulders.

* * * * *